(12) United States Patent
Gharpure et al.

(10) Patent No.: US 8,445,688 B2
(45) Date of Patent: May 21, 2013

(54) PROCESS FOR PRODUCING ENANTIOMER OF AMLODIPINE IN HIGH OPTICAL PURITY

(75) Inventors: Milind Moreshwar Gharpure, Maharashtra (IN); Baburao Manikrao Bhawal, Maharashtra (IN); Prasad Vasudeo Ranade, Maharashtra (IN); Rajendra Dagadu Deshmukh, Maharashtra (IN); Satish Ramanlal Mehta, Maharashtra (IN)

(73) Assignee: Emcure Pharmaceuticals Limited, Maharashtra (IN)

( * ) Notice: Subject to any disclaimer, the term of this patent is extended or adjusted under 35 U.S.C. 154(b) by 462 days.

(21) Appl. No.: 12/895,303

(22) Filed: Sep. 30, 2010

(65) Prior Publication Data

US 2011/0021783 A1 Jan. 27, 2011

Related U.S. Application Data

(62) Division of application No. 11/574,781, filed as application No. PCT/IB2005/003108 on Oct. 17, 2005, now Pat. No. 7,858,801.

(30) Foreign Application Priority Data

Oct. 20, 2004 (IN) .......................... 1123/MUM/2004

(51) Int. Cl.
*C07D 211/86* (2006.01)
(52) U.S. Cl.
USPC ........................................................ 546/321
(58) Field of Classification Search
USPC ........................................................ 546/321
See application file for complete search history.

(56) References Cited

U.S. PATENT DOCUMENTS

| 6,046,338 A | 4/2000 | Spargo |
| 6,057,344 A | 5/2000 | Young |
| 6,080,761 A | 6/2000 | Chahwala et al. |
| 6,608,206 B1 | 8/2003 | Joshi et al. |
| 6,646,131 B2 | 11/2003 | Zhang |
| 6,822,099 B2 | 11/2004 | Senanayake et al. |
| 7,202,365 B2 | 4/2007 | Chung et al. |
| 2003/0176706 A1 | 9/2003 | Joshi et al. |
| 2007/0155969 A1 | 7/2007 | Chung et al. |

FOREIGN PATENT DOCUMENTS

| EP | 0 331 315 A2 | 9/1989 |
| EP | 1 348 697 A1 | 10/2003 |
| EP | 1 407 773 A1 | 4/2004 |
| WO | WO 03/035623 A1 | 5/2003 |
| WO | WO 2004/024689 A1 | 3/2004 |

OTHER PUBLICATIONS

Arrowsmith, J.E. et al., "Long-Acting Dihydropyridine Calcium Antagonists. 1. 2-Alkoxymethyl Derivatives Incorporating Basic Substituents", Journal of Medical Chemistry, 1986, vol. 29, No. 9 pp. 1697-1702.

"Guide for Industry Impurities: Residual Solvents", U.S. Department of Health and Human Services Food and Drug Administration Center for Veterinary Medicine, Sep. 1999, p. 9.

*Primary Examiner* — Patricia L Morris
(74) *Attorney, Agent, or Firm* — Foley & Lardner LLP

(57) ABSTRACT

The present invention relates to a process for preparation of optically pure (S)-amlodipine-L-hemitartrate DMF solvate comprising the steps of treating (R,S) amlodipine base with L-tartaric acid in the presence of dimethyl formamide and a co-solvent. The invention also relates to a process for converting (R) or (S)-amlopidine-L-hemitartrate DMF solvate into their besylates without isolating free chiral amlopidine base after solution.

5 Claims, 1 Drawing Sheet

X-ray Diffraction of S-Amlodipine Besylate Hemi-pentahydrate
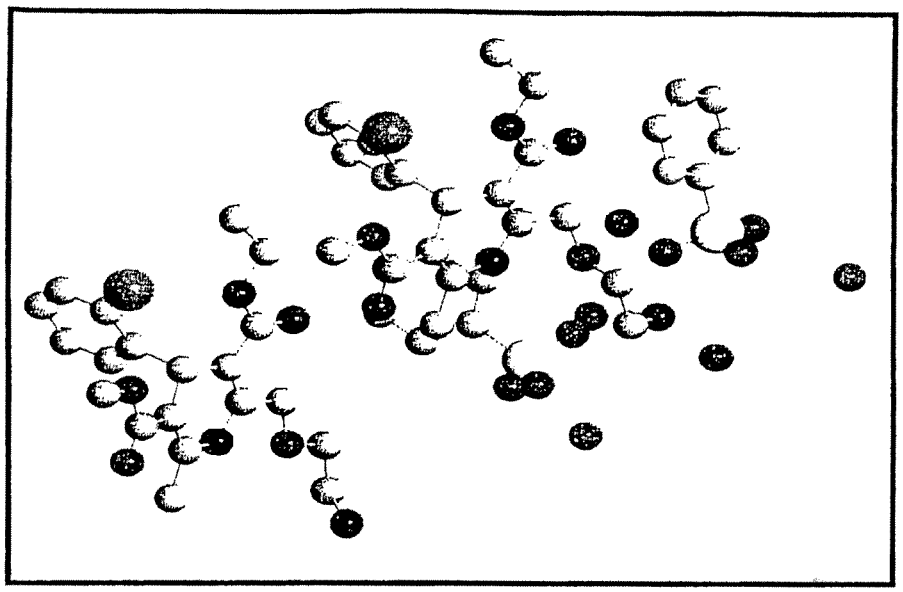

PROCESS FOR PRODUCING ENANTIOMER OF AMLODIPINE IN HIGH OPTICAL PURITY

CROSS-REFERENCE TO RELATED APPLICATIONS

This application is a Divisional of U.S. patent application Ser. No. 11/574,781, filed Dec. 21, 2007 now U.S. Pat. No. 7,858,801, which is the National Stage of International Patent Application No. PCT/IB2005/003108, filed Oct. 17, 2005, now published as WO 2006/043148, which in turn claims priority from Indian Patent Application No. 1123/MUM/2004, filed Oct. 20, 2004. The contents of these applications are incorporated herein by reference in their entirety.

TECHNICAL FIELD

This invention relates to a process for preparing optically active isomer of amlodipine of formula (1) in high optical purity and its pharmaceutically acceptable salts.

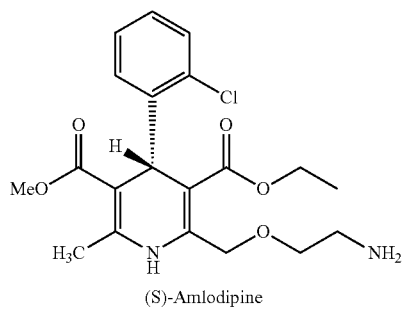

(S)-Amlodipine (1)

It further relates to the method for preparation of (S)-amlodipine-L-hemitartrate dimethyl formamide (DMF) solvate (2a) and (R)-amlodipine-L-hemitartrate DMF solvate (3a) from racemic (RS)-amlodipine free base using L-tartaric acid and their efficient separation and purification of salts in high optical purity. Further it also relates to the process of converting (S)-amlodipine-L-hemitartrate DMF solvate (2a) and (R)-amlodipine-L-hemitartrate DMF solvate (3a) into their pharmaceutically acceptable salts such as besylate, maleate, fumarate, succinate, oxalate etc. with or without isolating free chiral amlodipine base after resolution.

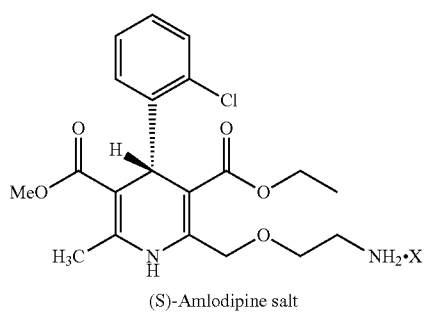

(S)-Amlodipine salt (2)

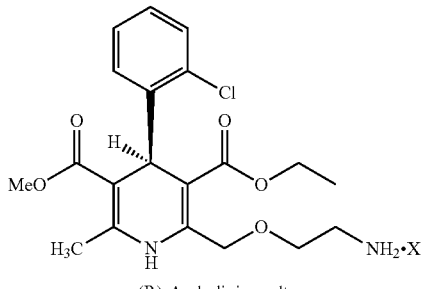

(R)-Amlodipine salt (3)

X = (a) 1/2 L-(+)-tartaric acid DMF solvate; (b) benzene sulphonic acid; (c) 1/2 maleic acid; (d) 1/2 fumaric acid; (e) 1/2 succinic acid; (f) 1/2 oxalic acid; (g) nicotinic acid; (h) camphor sulphonic acid etc.

BACKGROUND

Amlodipine and its salts are long lasting calcium channel blockers useful in the treatment of cardiovascular disorders. Racemic amlodipine is currently used as its besylate or maleate salt in the treatment of angina, hypertension and congestive heart failure. Amlodipine has a chiral centre at the 4-position of dihydropyridine ring and exists in two enantiomeric forms R and S, exhibiting different pharmacological profiles. The S-isomer is the more potent calcium channel blocker, while R-isomer has little or no calcium channel blocking activity. The utilization of optically pure (S)-amlodipine for treatment of hypertension and angina has been disclosed in U.S. Pat. No. 6,057,344.

R-(+)-amlodipine has little activity as a calcium channel blocker, but it is not pharmacologically inert, in fact it is a potent inhibitor of smooth muscle cell migration. (U.S. Pat. No. 6,080,761). Hence, the patients having specific therapeutic requirement of (S)-amlodipine need to be provided the pharmaceutical composition containing (S)-amlodipine, which is substantially free of (R)-amlodipine. There is presently no amlodipine product that contains S-(−)-amlodipine substantially free of the R-(+) enantiomer.

PRIOR ART

The enantiomerically pure amlodipine isomers were first prepared via separation of the diastereotopic azide ester intermediate of 2-methoxy-2-phenylethanol [J. E. Arrowsmith et al, J. Med. Chem. 29, 1696, 1986].

The separation of R and S amlodipine isomers was also achieved by the resolution of intermediate racemic azido acid cinchonidine salts, which were then eventually converted into the desired enantiomerically pure amlodipine (R) and (S) isomers [J. E. Arrowsmith et al, EP 0331315].

U.S. Pat. No. 6,046,338 has disclosed that resolution of racemic amlodipine base can be accomplished using L or D tartaric acid in dimethyl sulphoxide to respectively give R-(+)-amlodipine-L-hemitartrate and S(−)-amlodipine-D-hemitartrate [US2003176706; EP 1348 697]. This patent also mentions explicitly that DMSO is essential for the unique separation process.

Spargo described a process for the preparation of (S)-amlodipine-D-hemi-tartrate DMSO mono-solvate. Also, use of co-solvent in combination with DMSO is exemplified. FDA guidelines stipulate that the residual concentration of DMSO should not exceed 0.5% [Guidance for Industry impurities: residual solvents, FDA, September 1999, page 9].

However, use of DMSO in the final step i.e. resolution step, although undesired is unavoidable in most of the literature procedures.

The disadvantages associated with the process as disclosed in the prior art are:

1) Utilization of naturally occurring and economical L-tartaric acid for resolution of racemic amlodipine results in the separation of the undesired R(+) isomer of amlodipine, while the desired S(−) isomer passes into the mother liquor along with other impurities. The desired S(−) isomer has to be isolated by employing the more costly D-tartaric acid in a subsequent step, thereby making the overall process lengthy, uneconomical, and cumbersome.
2) Dimethyl sulphoxide is a solvent having an obnoxious odour and is therefore, unsuitable for utilization on an industrial scale, due to environmental concerns.
3) The high boiling point of dimethyl sulphoxide (183° C.), which could be present in isolated (S)-amlodipine, makes it very difficult to remove it from the final product during drying, thereby raising the level of organic volatile impurities in (S)-amlodipine and rendering it unsuitable for pharmaceutical use.

EP 1407773 and U.S. Pat. No. 6,608,206 disclose a process for the preparation of (S)-Amlodipine besylate, which comprises reacting (S)-Amlodipine free base with benzene sulfonic acid in an organic solvent.

This patent teaches a method only for the preparation of the acid addition salts of S(−) amlodipine from the free base and purification of such salts by recrystallization from isopropanol, but does not mention about the resolution of racemic amlodipine Further, U.S. Pat. No. 6,822,099 and WO 03/035623 describes resolution of racemic amlodipine base using L or D tartaric acid in dimethyl acetamide solvent.

This patent teaches a method for resolution of racemic amlodipine through the preparation of dimethyl acetamide solvate of L or D hemitartrate salt respectively of (R) or (S) isomer of amlodipine.

Herein also the (S)-isomer is resolved from the racemic mixture with the relatively costlier (D)-tartaric acid. The dimethyl acetamide solvate of (S)-amlodipine (D)-hemi-tartrate salt is obtained after stirring for 3-5 hours. The desired dimethyl acetamide solvate is isolated and converted to the desired acid addition salt through the formation of the free base after treatment with an inorganic base like sodium hydroxide.

The method embodied in U.S. Pat. No. 6,822,099 suffers from the following drawbacks:

a) utilization of costlier D-tartaric acid for resolution of racemic amlodipine since in prior art only the (S) isomer of amlodipine precipitates with D-tartaric acid and not with L-tartaric acid.
b) Utilization of the naturally occurring relatively cheaper L-tartaric acid leads to the precipitation of the undesired (R)-isomer of Amlodipine while the desired (S)-isomer has to be isolated from the mother liquor, which has already carried all the impurities of the undesired (R)-isomer.

Yet another patent WO 2004/024689 describes resolution of racemic amlodipine base using L or D tartaric acid and dimethyl sulphoxide as solvent.

This patent teaches a method for resolution of racemic amlodipine by utilizing dimethyl sulphoxide and L-tartaric acid. In this method the undesired (R)-isomer of amlodipine first precipitates out as the L-hemi tartrate salt, while the desired (S)-isomer along with impurities passes into the mother liquor.

The desired (S)-amlodipine is precipitated from the mother liquor by addition of an organic solvent like dichloromethane. The (S)-amlodipine hemi-L-tartrate salt is then desolvated by refluxing in an organic solvent like methanol and neutralised by the addition of a solution of an inorganic base.

This method although using the relatively cheap L-tartaric acid for resolution of racemic amlodipine has several drawbacks, which makes the process unviable for commercialization, one being that S-amlodipine-L-hemitartrate is to be isolated from mother liquor, which itself contains many impurities.

a) (S)-amlodipine is not obtained directly after addition of L-tartaric acid to the mixture of racemic amlodipine and DMSO, rather (S)-amlodipine hemi-L-tartrate DMSO solvate has to be isolated from the mother liquor, which in addition to (S)-amlodipine also contains other impurities. Thus there is every chance that some of these impurities present in the mother liquor will be carried forward into (S)-amlodipine solid during precipitation with an organic solvent like dichloromethane.
b) The process for obtaining (S)-amlodipine is lengthy and cumbersome, since it involves three steps, viz.
  i) addition of L-tartaric acid and filtering the resulting precipitate,
  ii) precipitating the desired (S)-amlodipine hemi-L-tartrate DMSO solvate along with part of undesired isomer as well as other impurities, which is a general flaw in obtaining the desired enantiomer from the filtrate,
  iii) treating (S)-amlodipine hemi-L-tartrate DMSO with a base to obtain (S)-amlodipine free base.
c) Utilization of a solvent like dimethyl sulfoxide, which has an obnoxious bad odour and is not suitable for industrial use.

U.S. Pat. No. 6,646,131 discloses the utilization of hexa-deuterium dimethyl sulphoxide (DMSO-$d_6$) in conjunction with D or L tartaric acid for separation of the (R) and (S) isomers in amlodipine.

This method is not suitable for industrial use, since hexa-deuterium dimethyl sulphoxide is very costly. Further, hexa-deuterium dimethyl sulphoxide being hygroscopic in nature has got a tendency of degrading into non-deuterated dimethyl sulfoxide either during storage or usage. Further, in this case also, the relatively costlier D-tartaric acid is required for precipitation of the desired (S)-isomer of amlodipine.

The main disadvantages of the prior art are the use of either expensive resolving agents such as synthetic D-tartaric acid or camphor sulphonic acid. or lack of suitability for industrial application.

Further, the use of L-tartaric acid has also been disclosed for the preparation of (S)-amlodipine-L-hemi-tartrate [US 2003176706 and EP 1348697]. However, the enantiomeric purity of (S)-amlodipine obtained by this method is only about 97% ee. Moreover, this method involves use of total required quantity of tartaric acid (0.5 equivalent) in beginning of the reaction, subsequent isolation of precipitated (R)-amlodipine-L-hemitartrate followed by isolation of precipitated (S)-amlodipine-L-hemitartrate from filtrate by the sequential filtration.

Thus, by use of dimethyl acetamide or dimethyl sulfoxide solvent, initial precipitation of R-isomer cannot be avoided. The precipitation of (R) isomer being first and removal of the same in 100% being a challenging task, the remaining (R) isomer gets precipitated in eventual crystallization, rendering the poor enantiomeric purity of (S) isomer. Thus, use of this method for the resolution of amlodipine base into its enantiomers on large scale gave unsatisfactory results in terms of both yield and enantiomeric purity. Hence, there is a long-felt need to develop the economical, industrially applicable, process of resolution, whereby S-amlodipine solvate is preferentially isolated in high enantiomeric purity.

OBJECTS OF THE INVENTION

The main object of the invention is to provide an industrially viable method for preparing S-amlodipine solvate and R-amlodipine solvate in high enantiomeric purity by using easily accessible and a more economical reagent.

Another object of the invention is to preferentially isolate S-amlodipine solvate, after addition of L-tartaric acid to racemic amlodipine instead of having to isolate (S)-amlodipine-L-hemitartrate solvate from the mother liquor.

Yet another object of the invention is to provide a cost-effective and industrially viable method for preparation of (S)-amlodipine of high purity by reducing the processing time and hence the each batch cycle, manpower, utilities, reactor occupancy etc.

Still another object of the invention is to provide single enantiomer of amlodipine-L-hemitartrate DMF solvate.

Further objective of this invention is to provide a method for conversion of chirally pure (S)-amlodipine base or its tartrate into its pharmaceutically acceptable salts.

DESCRIPTION OF THE INVENTION

One aspect of the invention relates to a process for preparing (S)-amlodipine-L-hemitartrate DMF solvate in high optical purity and in good yield by treating (R,S) amlodipine base with a tartaric acid selected from D-tartaric acid and L-tartaric acid, in the presence of dimethyl formamide and a co-solvent.

Further, adding D or L tartaric acid in excess to the reaction mixture above yields R-amlodipine-L-hemitartrate DMF solvate.

Thus, the invention provides a simple, economically viable and efficient process for preparing a solvate of amlodipine and their pharmaceutically acceptable salts in good yield with high enantiomeric purity (>99% de). Accordingly, the invention provides an excellent tool for industrial production of S-amlodipine solvates and salts.

For obtaining resolution of racemic amlodipine with L-tartaric acid to give (S)-amlodipine were tried out with several solvents belonging to different classes, such as ketones (acetone, methyl ethyl ketone, and methyl isobutyl ketone); alcohols (methanol, ethanol, isopropanol, n-butanol); esters (ethyl acetate, isopropyl acetate, butyl acetate); ethers (diethyl ether, diisopropyl ether, tetrahydrofuran); chlorinated hydrocarbons (dichloromethane, chloroform); hydrocarbons (toluene, cyclohexane); amides (dimethyl formamide, dimethyl acetamide); and acetonitrile.

When performing certain routine experiments, the inventors surprisingly found that use of dimethyl formamide, a solvent yielded (S)-amlodipine solvate of optical purity of more than 76%, while dimethyl acetamide, which is reported in prior art yields (S)-amlodipine of 49.39% optical purity. The said finding of the present inventors in the case of dimethyl acetamide was very much surprising and completely contrary to that reported in prior art.

Therefore, further work was carried out with dimethyl formamide, with the intention of improving the optical purity of S-amlodipine. The inventors surprisingly found that use of a co-solvent in combination with dimethyl formamide yields S-amlodipine solvate in very high purity of at least greater than 95%. Hence, resolution of racemic amlodipine was carried out with DMF in combination with a co-solvent.

Accordingly, racemic (RS)-amlodipine free base is treated with L-tartaric acid in dimethyl formamide (DMF) or in combination with a co-solvent. The co-solvent may be selected from the group comprising of water, alcohols, esters, amides, halogenated solvents, hydrocarbons, etc. Preferred alcohol is straight chain saturated alcohol. The preferred alcohol is methanol. Preferred chlorinated solvent is dichloromethane and preferred aliphatic hydrocarbon is hexane.

Further, during the investigations progressed, it was noticed that when L-tartaric acid dissolved in a mixture of dimethyl formamide and co-solvent was added to the mixture of racemic amlodipine in dimethyl formamide co-solvent mixture, the outcome was completely surprising. It was the (S)-amlodipine hemitartrate salt, which precipitated out first instead of (R)-amlodipine hemitartrate, which is expected and generally reported in prior art. Further, the said (S)-amlodipine hemitartrate salt, isolated as DMF solvate was obtained with high optical purity (of greater than 98%).

The main advantage is that now, by virtue of the invented process, the compound S-amlodipine hemi-tartarate solvate may be obtained in a single shot, which is economical and without use of complicated procedures. Further, there is no loss of product either as it is obtained as the first product.

Further, when dimethyl formamide is used along with water, the yield of S-amlodipine besylate is 80-95%.

Addition of 0.20 to 0.30 equivalent preferably 0.25 to 0.3 equivalent of L-tartaric acid either as such or as a mixture with dimethyl formamide alone or dimethyl formamide/co-solvent mixture ensured that only (S)-amlodipine-L-hemitartrate DMF solvate is formed preferentially. The chiral purity of (S)-amlodipine-L-hemitartrate DMF solvate is found to be pharmaceutically acceptable. The mother liquor thus gets enriched with R-isomer, from which is isolated (R)-amlodipine-L-hemitartrate-DMF solvate by additional use of 0.2 to 0.25 equivalent of L-tartaric acid. The high diastereomeric purity of S-amlodipine-L-hemitartrate can be achieved by optionally using appropriate co-solvent to yield S-isomer enriched hemi-L-tartrate DMF solvate from above referred organic solvents. The pharmaceutically acceptable salts of amlodipine, for example the amlodipine besylate salt is obtained by addition of benzene sulphonic acid to the (S)-Amlodipine-L-hemitartrate DMF solvate in an aqueous medium or in a mixture of an organic solvent and water to give (S)-amlodipine besylate (hydrate)$_n$ wherein n=½ 1 to 3, preferably hemi-pentahydrate or dihydrate of (S)-amlodipine besylate salt.

Alternatively, addition of 0.25 to 0.3 equivalent of D-tartaric acid ensures that only (R)-amlodipine-D-hemitartrate-DMF solvate is formed preferentially. The chiral purity of (R)-amlodipine-D-hemitartrate is found to be >99% de. The mother liquor thus gets enriched with S-isomer, from which is isolated (S)-amlodipine-D-hemi-tartrate-DMF solvate salt (90% de) by additional use of 0.2 to 0.25 equivalent of D-tartaric acid. The high diastereomeric purity (>99% de) for example of R-amlodipine-D-hemitartrate is achieved by temperature dependent sequential crystallization of enriched hemitartrate DMF solvate from alcoholic solvents such as methanol, ethanol, n-propanol, isopropanol and mixture thereof etc. preferably methanol and/or ethanol.

The amount of DMF/water mixture for resolution of amlodipine may be 9-13 times. The amount of the organic solvent in DMF/co-solvent mixture may be 14-16%. The preferred amount of co-solvent is 15%.

The chirally pure R and S amlodipine-L-hemitartrate salts may optionally be converted into their respective free bases by the treatment of bases such as aqueous. ammonia solution, and alkali metal hydroxides such as NaOH, KOH at 20-35° C. The pharmaceutically useful salts of R and S amlodipine are prepared either from their respective tartrate salts or their free bases with acids, such as benzene sulphonic acid, nicotinic acid, succinic acid, maleic acid, fumaric acid, oxalic acid, camphor-10-sulphonic acid, etc.

According to the instant invention, the process for the preparation of chirally pure (S)-amlodipine-L-hemitartrate and (R)-amlodipine-L-hemitartrate comprises the steps of:

i) preparing mixture of L-tartaric acid or D-tartaric acid and (RS)-amlodipine in DMF with a co-solvent;

ii) filtering the solid obtained of (S)-amlodipine-L-hemitartrate-DMF-solvate or (R)-amlodipine-D-hemi-tartrate-DMF-solvate;

iii) optionally adding excess of the previously added enantiomer of tartaric acid to the mother liquor from step (ii) and filtering (R)-amlodipine-L-hemitartrate-DMF-solvate or (S)-amlodipine-D-hemitartrate-DMF-solvate.

The co-solvent referred above may be inorganic solvent or organic solvent. The inorganic co-solvent is water.

I) Resolution of Racemic Amlodipine with L-Tartaric Acid in Presence of Aqueous Dimethyl Formamide It was found that resolution of racemic amlodipine was achieved when aqueous dimethyl formamide was employed as solvent.

Effect of Water in Dimethyl Formamide on the Resolution of Racemic Amlodipine.

The present inventors during the course of investigation found that dimethyl formamide when employed alone does not lead to complete resolution of racemic amlodipine. Resolution of racemic amlodipine is accomplished only when water (one of the co-solvents) in the range of 2 to 50% (v/v) is added to dimethyl formamide.

The preferred amount of water is between 8 and 20% (v/v) in the total volume of the dimethyl formamide/water mixture The more preferred amount of water added to dimethyl formamide for resolution was between 10% and 15% to get high enantiomeric purity.

Also, the purity of (S) amlodipine obtained depends upon the dilution of the reaction mixture. The dilution of the reaction mixture is preferably 9 to 13 times of racemic amlodipine base.

The resolution can be carried out at a temperature between 24° C. and 40° C., preferably between 24° C. and 28° C.

II) Resolution of Racemic Amlodipine, in Presence of Dimethyl Formamide and an Organic Solvent.

The instant invention also provides a method wherein the resolution of racemic amlodipine can also be achieved when dimethyl formamide is used in conjunction with other organic solvents as co-solvent.

The co-solvent was selected from the group comprising of alcohols, esters, amides, halogenated solvents, hydrocarbons etc.

The effect of the co-solvent in the dimethyl formamide mixture on the resolution of racemic amlodipine-L-hemitartrate salt has been described in Table-I for better understanding.

Table-I: Effect of co-solvent in dimethyl formamide binary mixture on the resolution of racemic amlodipine.

| No. | Co-solvent with Dimethyl formamide as a 15% mixture | Optical purity of (S)-Amlodipine (%) | % Yield |
|---|---|---|---|
| 1. | Methanol | 99.70 | 42.37 |
| 2. | Dichloromethane | 99.38 | 52.9 |
| 3. | n-Hexane | 99.97 | 31.77 |
| 4. | Ethyl acetate | 99.37 | 21.18 |
| 5. | Note: Without the co-solvent, the optical purity of (S)-amlodipine-L-hemitartrate DMF solvate is only 76%, with yield of 96.25% (w/w). | | |

It was found that the optical purity of (S)-amlodipine-L-hemitartrate DMF solvate is also dependent on the amount of the organic solvent The amount of organic co-solvent in the DMF/co-solvent mixture that was required for getting optical purity in a single or subsequent crystallization was between 3 and 30% volume in the total volume of DMF/co-solvent mixture.

The preferred volume of the organic solvents was however between 12 and 18% (v/v) of the total volume of the dimethyl formamide/co-solvent mixture.

For obtaining desired purity, the different parameters, which can be varied, are temperature of the mixture, time for crystallization, concentration of mixture, seeding of the mixture etc.

The (S)-amlodipine-L-hemitartrate DMF solvate, which thus isolated was confirmed by $^1$H NMR spectra (presence of 2 methyl signals from DMF) was then converted to its pharmaceutically acceptable acid addition salt preferably the besylate salt and its hydrates by any of the methods described below. The $^1$H NMR spectra of (S)-amlodipine-L-hemitartrate DMF solvate showed the following values, which confirmed its identity as (S)-amlodipine-L-hemitartrate DMF solvate.

$^1$H N.M.R(CDCl$_3$): 8.01 (s, 1H, CHO); 7.04-7.41 (m, 4H), 5.40 (s, 1H); 4.72 (qq, 2H), 4.36 (s, 1H), 4.02 (m, 2H); 3.77 (m, 2H), 3.57 (s, 3H), 3.28 (m, 2H), 3.0 (s, 3H; DMF); 2.8 (s, 3H; DMF); 2.31 (s, 3H), 1.15 (t, 3H)

The (S)-amlodipine besylate hemi-pentahydrate salt was prepared from (S)-amlodipine-L-hemitartrate dimethyl formamide solvate by treating with benzene sulphonic acid in a mixture of an organic solvent and water.

(S)-Amlodipine-L-hemi-tartrate DMF solvate was added to water.

An organic solvent, which is preferably an alcohol, was added to the mixture.

The alcohol was selected from the group comprising of methanol, ethanol, n-propanol, isopropanol, n-butanol, secondary butanol, tertiary butanol etc. The preferred alcohol was isopropanol.

The volume of isopropanol added was between 0.90 volume and 1.5 volumes per gram of the (S)-amlodipine hemitartrate DMF solvate.

Benzene sulphonic acid dissolved in water was added to the (S)-amlodipine hemi-tartrate DMF solvate.

The amount in moles of benzene sulphonic acid added was between 2.0 and 2.3 moles equivalent per mole of (S)-amlodipine-L-hemitartrate dimethyl formamide solvate.

The amount of water employed for dissolving benzene sulphonic acid was between 0.90 volumes and 1.50 volumes per gram of (S)-amlodipine hemitartrate DMF solvate.

The resultant mixture after addition of aqueous benzene sulphonic acid solution was agitated at ambient temperature for 10-30 minutes. Water was further added to the mixture for complete precipitation of the (S)-amlodipine besylate salt.

The amount of water added was five volumes of water per gram of (S)-amlodipine hemitartrate DMF solvate. The reaction mixture was further stirred for 15 to 60 minutes for complete precipitation of the (S)-amlodipine besylate salt.

The diffraction scanning calorimetric analysis of (S)-amlodipine hemi-pentahydrate besylate salt thus prepared showed an endotherm at 71.9° C. and has moisture content between 7.0% and 8.0%. The single crystal X-ray diffraction analysis indicated that the (S)-amlodipine besylate had five molecules of water shared by two molecules of (S)-amlodipine besylate, which means that there are 2.5 molecules of water for one molecule of (S)-amlodipine besylate, hereby indicating that a hemi-pentahydrate solvate of (S)-amlodipine besylate salt was obtained. The same is shown in FIG. 1.

The 2θ values for the single-crystal spectra of (S)-amlodipine besylate hemipentahydrate solvate are as follows:

| 2θ values of (S)-amlodipine besylate hemipentahydrate | Intensity % |
|---|---|
| 3,315 | 73.5 |
| 6,669 | 70.1 |
| 7,487 | 6.8 |
| 8,225 | 10.3 |
| 10,039 | 100.0 |
| 10,772 | 8.3 |
| 12,276 | 44.1 |
| 12,956 | 25.0 |
| 13,501 | 39.0 |
| 13,993 | 45.3 |
| 14,448 | 8.6 |
| 15,006 | 34.5 |
| 15,650 | 5.7 |
| 16,586 | 14.6 |
| 17,207 | 19.9 |
| 18,871 | 8.9 |
| 19,806 | 14.7 |
| 20,199 | 45.0 |
| 20,684 | 10.2 |
| 21,470 | 21.3 |
| 21,730 | 37.6 |
| 22,964 | 27.4 |
| 23,709 | 48.3 |
| 24,936 | 37.2 |
| 27,032 | 30.7 |
| 27,968 | 11.8 |
| 34,002 | 10.5 |
| 35,473 | 7.9 |
| 35,986 | 6.2 |
| 38,412 | 7.8 |

(S)-Amlodipine besylate hemi-pentahydrate solvate salt thus prepared can also be converted into its besylate dihydrate salt by a simple method as mentioned below.

(S)-Amlodipine besylate hemi-pentahydrate salt was added to water. The amount of water in volume was between 20 times and 25 times volume per gram of the (S)-amlodipine besylate hemi-pentahydrate salt.

The mixture was heated to a temperature between 55° C. and 65° C. for 15-30 minutes.

The mixture was cooled to ambient temperature and the product allowed crystallizing completely over duration of 8-12 hours.

The mixture was then filtered, dried.

(S)-Amlodipine besylate salt thus obtained had moisture content between 5.85% and 6.0%, which corresponds to the dihydrate of (S)-amlodipine besylate.

(S)-Amlodipine besylate dihydrate can also be prepared from (S)-Amlodipine-L-hemitartrate dimethyl formamide (DMF) solvate by the following method.

(S)-Amlodipine-L-hemitartrate dimethyl formamide (DMF) solvate was added to water.

The amount of water utilized per gram of (S)-Amlodipine-L-hemitartrate dimethyl formamide (DMF) solvate was between 20 volumes and 25 volumes per gram of (S)-Amlodipine-L-hemitartrate dimethyl formamide (DMF) solvate.

Benzene sulphonic acid dissolved in water was added to the (S)-amlodipine-L-hemi-tartrate DMF solvate.

The amount in moles of benzene sulphonic acid added was between 2.0 and 2.3 moles per mole of the (S)-amlodipine-L-hemitartrate DMF solvate.

The amount of water employed for dissolving benzene sulphonic acid was between 1.25 and 1.50 volumes per gram of (S)-amlodipine-L-hemitartrate DMF solvate.

The mixture thus obtained was heated to a temperature between 55° C. and 65° C. The preferred temperature was 60±2° C.

The solution was cooled for complete crystallization of (S)-amlodipine besylate dihydrate salt.

The besylate salt was filtered, washed with water and dried to give (S)-amlodipine besylate salt having moisture content between 5.85% and 6.00%.

The process of present invention is described herein below with reference to examples, which are illustrative only and should not be construed to limit the scope of the present invention in any manner.

BRIEF DESCRIPTION OF THE ACCOMPANYING DRAWINGS

FIG. 1: X-ray Diffraction of S-Amlodipine Besylate Hemipentahydrate

 Corresponds to chlorine atoms.

 Corresponds to Oxygen atoms.

 Corresponds to Nitrogen atoms.

 Corresponds to Sulphur atoms.

 Corresponds to Carbon atoms.

Molecular formula of S(−) Amlodipine besylate is $C_{20}H_{25}ClN_2O_5 \cdot C_6H_6SO_3$. The single crystal attached here is showing $C_{40}H_{50}Cl_2N_4O_{10} \cdot C_{12}H_{12}S_2O_6 \cdot 5H_2O$. This clearly indicates that five molecules of water are shared by two molecules of S(−) Amlodipine besylate.

EXAMPLE 1

(S)-Amlodipine-L-hemitartrate dimethyl formamide solvate (RS)-Amlodipine (16 gm, 0.04 moles) was dissolved in 140 ml dimethyl formamide water mixture (15% water in DMF).

To this mixture, a solution of L-tartaric acid, prepared by dissolving tartaric acid (1.47 g, 0.01 moles) in 20 ml DMF+ water mixture (proportion as referred above) was added drop wise in 30 min. The mixture was stirred for 4 hr at room temperature after addition. The slurry was filtered and the residual solid was washed with acetone (10 ml) and dried to give the title product.

Yield=7.8 gm.

% Yield: 82.62%.

Melting point; 137° C.

Optical Purity by Chiral HPLC: 99.00%.

EXAMPLE 2

(S)-Amlodipine-L-hemitartrate dimethyl formamide solvate (RS)-Amlodipine (16 gm, 0.04 moles) was dissolved in 140 ml dimethyl formamide water mixture (20% water in DMF).

To this mixture, a solution of L-tartaric acid, prepared by dissolving tartaric acid (1.47 g, 0.01 moles) in 20 ml DMF+water mixture (proportion as referred above) was added drop wise in 30 min. The mixture was stirred for 4 hr at room temperature after addition. The slurry was filtered and the residual solid was washed with acetone (10 ml) and dried to give the title product.

Yield=9.0 gm.
% Yield: 95.3%
Optical Purity by Chiral HPLC: 98.86%

EXAMPLE 3

(S)-Amlodipine-L-hemitartrate dimethyl formamide solvate (RS)-Amlodipine (16 gm, 0.04 moles) was dissolved in 220 ml dimethyl formamide water mixture (10% water in DMF).

To this mixture, a solution of L-tartaric acid, prepared by dissolving tartaric acid (1.47 g, 0.01 moles) in 20 ml DMF+water mixture (proportion as referred above) was added drop wise in 30 min. The mixture was stirred for 4 hr at room temperature after addition. The slurry was filtered and the residual solid was washed with acetone (10 ml) and dried to give the title product.

Yield=9.0 gm.
% Yield: 95.3%
Optical Purity by Chiral HPLC: 98.69%.

EXAMPLE 4

(S)-Amlodipine-L-hemitartrate dimethyl formamide solvate (RS)-Amlodipine (16 gm, 0.04 moles) was dissolved in 140 ml dimethyl formamide water mixture (15% water in DMF).

To this mixture, a solution of L-tartaric acid, prepared by dissolving tartaric acid (1.47 g, 0.01 moles) in 20 ml DMF+water mixture (proportion as referred above) was added drop wise in 30 min. The mixture was stirred for 1.5 hr at room temperature after addition. The slurry was filtered and the residual solid was washed with acetone (10 ml) and dried to give the title product.

Yield=8.0 gm.
% Yield: 84.74%
Melting point; 137° C.
Optical Purity by Chiral HPLC: 99.94%

EXAMPLE 5

(S)-Amlodipine-L-hemitartrate dimethyl formamide solvate (RS)-Amlodipine (16 gm, 0.04 moles) was dissolved in 140 ml dimethyl formamide methanol mixture (15% methanol in DMF).

To this mixture, a solution of L-tartaric acid, prepared by dissolving tartaric acid (1.47 g, 0.01 moles) in 20 ml DMF+methanol mixture (proportion as referred above) was added drop wise in 30 min. The mixture was stirred for 4 hr at room temperature after addition. The slurry was filtered and the residual solid was washed with acetone (10 ml) and dried to give the title product.

Yield: 4.0 gms (w/w)
% Yield: 42.37%.
Melting point; 137° C.
Optical Purity by Chiral HPLC: 99.70%.

EXAMPLE 6

(S)-Amlodipine-L-hemitartrate dimethyl formamide solvate (RS)-Amlodipine (16 gm, 0.04 moles) was dissolved in 140 ml dimethyl formamide dichloromethane mixture (15% dichloromethane in DMF).

To this mixture, a solution of L-tartaric acid, prepared by dissolving tartaric acid (1.47 g, 0.01 moles) in 20 ml DMF+dichloromethane mixture (proportion as referred above) was added drop wise in 30 min. The mixture was stirred for 4 hr at room temperature after addition. The slurry was filtered and the residual solid was washed with acetone (10 ml) and dried to give the title product.

Yield: 5.0 gms (w/w)
% Yield: 52.9%.
Melting point; 137° C.
Optical Purity by Chiral HPLC: 99.38%

EXAMPLE 7

(S)-Amlodipine-L-hemitartrate dimethyl formamide solvate (RS)-Amlodipine (16 gm, 0.04 moles) was dissolved in 140 ml dimethyl formamide hexane mixture (15% hexane in DMF).

To this mixture, a solution of L-tartaric acid, prepared by dissolving tartaric acid (1.47 g, 0.01 moles) in 20 ml DMF+hexane mixture (proportion as referred above) was added drop wise in 30 min. The mixture was stirred for 4 hr at room temperature after addition. The slurry was filtered and the residual solid was washed with acetone (10 ml) and dried to give the title product.

Yield: 3.0 gms.
% Yield: 31.77%.
Melting point; 137° C.
Optical Purity by Chiral HPLC: 99.97%.

EXAMPLE 8

(S)-Amlodipine-L-hemitartrate dimethyl formamide solvate (RS)-Amlodipine (16 gm, 0.04 moles) was dissolved in 140 ml dimethyl formamide ethyl acetate mixture (15% ethyl acetate in DMF).

To this mixture, a solution of L-tartaric acid, prepared by dissolving tartaric acid (1.47 g, 0.01 moles) in 20 ml DMF+ethyl acetate mixture (proportion as referred above) was added drop wise in 30 min. The mixture was stirred for 4 hr at room temperature after addition. The slurry was filtered and the residual solid was washed with acetone (10 ml) and dried to give the title product.

Yield: 2.0 gms
% Yield: 21.18%.
Melting point; 137° C.
Optical Purity by Chiral HPLC: 99.37%.

EXAMPLE 9

(R)-Amlodipine-D-hemitartrate dimethyl formamide solvate (RS)-Amlodipine (16 gm, 0.04 moles) was dissolved in 140 ml dimethyl formamide water mixture (15% water in DMF).

To this mixture, a solution of D-tartaric acid, prepared by dissolving tartaric acid (1.47 g, 0.01 moles) in 20 ml DMF+ water mixture (proportion as referred above) was added drop wise in 30 min. The mixture was stirred for 4 hr at room temperature after addition. The slurry was filtered and the residual solid was washed with acetone (10 ml) and dried to give the title product.

Yield=7.4 gm.
% Yield: 78.38%.
Melting point; 137° C.
Optical Purity by Chiral HPLC: 99.50%

EXAMPLE 10

Preparation of (S)-amlodipine besylate hemi-pentahydrate salt from (S)-amlodipine-L-tartrate DMF solvate (S)-Amlodipine-L-hemitartrate DMF solvate (1000 gms; 1.034 moles) was added to distilled water (5500 ml). Isopropyl alcohol (1000 ml) was added to the mixture and stirred for 10 minutes. Benzene sulphonic acid (327 gms; 2.068 moles) was dissolved in distilled water (1000 ml) and added to the mixture, at ambient temperature. The reaction mixture was stirred for 10-15 minutes for complete formation of the besylate salt. Distilled water (5000 ml) was added to the mixture in 15-30 minutes and stirred further for 30 minutes for complete precipitation of the besylate salt. (S)-amlodipine besylate was filtered, washed with distilled water and then with cyclohexane (1000 ml). The product was dried at 35-40° C.

Yield: 1000 gms
Chemical purity: 99.5%
Optical purity: >99%.
Water content: 7.0%-8.0%. The same is confirmed by elemental analysis.
I.R spectra: 3347-3521 (—NH stretching), 2898-3057 (—OH stretching); 1684 (—C═O stretching), 1603 (—NH; primary amine), 1481 (—NH; secondary amine), 1198 (—$CH_2$—O—$CH_2$—; ether linkage)
DSC analysis: 71.9° C.

EXAMPLE 11

Preparation of (S)-Amlodipine besylate dihydrate from (S)-Amlodipine-L-hemi-tartrate DMF solvate (S)-Amlodipine hemi-tartarate DMF solvate (200 g) was mixed with water (4500 ml). Benzene sulphonic acid (65.4 g) solution in water (300 ml) was added to it and stirred, which was heated to 60° C. under nitrogen atmosphere, the solution was cooled to room temperature and crystallized overnight. The solid was collected by filtration, washing with water (1000 ml), to give (S)-Amlodipine besylate, which was dried at room temperature to constant weight.

Yield: 264 g.
Water content: 5.85% to 6.0%.
Optical Purity: ≧99%.

EXAMPLE 12

Preparation of (S)-Amlodipine besylate dihydrate from (S)-Amlodipine hemi-pentahydrate (S)-Amlodipine hemi-pentahydrate (200 gms) was mixed with water (4800 ml). The mixture was heated to 60° C. under nitrogen atmosphere for 15-30 minutes. The mixture was then gradually cooled to room temperature and (S)-amlodipine dihydrate was then allowed to crystallize completely over duration of 8-12 hours. The separated product was filtered and dried at ambient temperature.

Yield: 180 gms
Water content: 5.85-6.00%.
Optical Purity: ≧99%.

EXAMPLE 13

Preparation of (R)-Amlodipine-L-hemitartrate DMF solvate

L-tartaric acid (1.47 gms; 0.01 moles) was added to the mother liquor obtained from Example 1. and stirred at ambient temperature for 240-300 minutes, till complete precipitation of the product The title compound was then filtered and dried.

Yield: 6.4 gms.
% Yield; 67.7%.

EXAMPLE 14

Preparation of (R)-Amlodipine-D-hemitartrate DMF solvate

D-tartaric acid (1.47 gms; 0.01 moles) was added to the mother liquor obtained from Example 1. and stirred at ambient temperature for 240-300 minutes, till complete precipitation of the product. The title compound was then filtered and dried.

Yield: 6.4 gms.
% Yield; 67.7%.

The advantages of the process of the present invention are:
A) The required (S)-Amlodipine-L-hemi-tartrate DMF solvate is precipitated first and not required to be precipitated from the mother liquor, thus avoiding presence of undesired isomer and the other impurities;
B) Resolution is done using less expensive, natural tartaric acid i.e. L-tartaric acid for obtaining (S)-amlodipine to make the process more economical and feasible on industrial scale;
C) The processing time, manpower, utilities etc., otherwise needed for obtaining (S)-enantiomer from the filtrate or mother liquor are avoided by developing a process, wherein the desired salt is obtained by first filtration, instead of obtaining from mother liquor;
D) Optical purity obtained is high with minimal chance of contamination of the unwanted R-isomer;
E) The isolation of the desired isomer is preferential and during the first filtration itself;
F) The time cycle/efforts/utilities/reactor occupancy etc. are desirable for the industrial purposes;
G) The purification process offers enantiomerically highly pure S-isomer in a single crystallization.

The invention claimed is:

1. A process for the preparation of (S)amlodipine besylate hemi-pentahydrate salt, comprising the steps of mixing (S)-amlodipine-L-hemitartrate DMF solvate with a mixture of water and an organic solvent, and adding an aqueous solution of benzene sulphonic acid.

2. A process as claimed in claim 1, further comprising adding water to the reaction mixture and filtering the hydrate.

3. A process as claimed in claim 1, wherein the organic solvent is an alcohol.

4. A process as claimed in claim 3, wherein the alcohol is selected from the group comprising of methanol, ethanol, n-propanol, isopropanol, n-butanol, secondary butanol and tertiary butanol.

5. A process as claimed in claim 4, wherein the alcohol is isopropanol.

* * * * *